(12) United States Patent
Weston

(10) Patent No.: US 8,425,468 B2
(45) Date of Patent: Apr. 23, 2013

(54) SAFETY NEEDLE ACCESSORY

(75) Inventor: Terence Edward Weston, Norfolk (GB)

(73) Assignee: Salvus Technology Limited, Stradbroke, Suffolk (GB)

( * ) Notice: Subject to any disclaimer, the term of this patent is extended or adjusted under 35 U.S.C. 154(b) by 431 days.

(21) Appl. No.: 12/527,575

(22) PCT Filed: Aug. 6, 2007

(86) PCT No.: PCT/US2007/017455
§ 371 (c)(1),
(2), (4) Date: Aug. 27, 2009

(87) PCT Pub. No.: WO2008/016710
PCT Pub. Date: Feb. 7, 2008

(65) Prior Publication Data
US 2010/0076382 A1    Mar. 25, 2010

(30) Foreign Application Priority Data
Aug. 4, 2006   (GB) .................................. 0615589.9

(51) Int. Cl.
*A61M 5/32*   (2006.01)

(52) U.S. Cl.
USPC ......................................... 604/198; 604/110

(58) Field of Classification Search .......... 604/192–198, 604/110, 181, 187
See application file for complete search history.

(56) References Cited

U.S. PATENT DOCUMENTS

| 4,664,654 | A | * | 5/1987 | Strauss ......................... 604/198 |
| 4,850,996 | A |   | 7/1989 | Cree |
| 5,336,197 | A |   | 8/1994 | Kuracina et al. |
| 5,658,256 | A | * | 8/1997 | Shields ......................... 604/192 |
| 5,810,784 | A | * | 9/1998 | Tamaro ......................... 604/263 |
| 6,536,805 | B2 | * | 3/2003 | Matkovich ....................... 285/3 |
| 2004/0210196 | A1 | | 10/2004 | Bush, Jr. et al. |
| 2005/0038391 | A1 | | 2/2005 | Wittland et al. |

FOREIGN PATENT DOCUMENTS

| EP | 0744183 A2 | 11/1996 |
| EP | 0815884 A1 | 1/1998 |
| FR | 2701848 A1 | 9/1994 |
| WO | 9419036 A1 | 9/1994 |
| WO | 2004/071560 A1 | 8/2004 |
| WO | 2006/090118 A1 | 8/2006 |

* cited by examiner

*Primary Examiner* — Kevin C Sirmons
*Assistant Examiner* — Phillip Gray
(74) *Attorney, Agent, or Firm* — Panitch Schwarze Belisario & Nadel LLP

(57) ABSTRACT

A safety needle accessory includes a hub (6) having a connector (2) for surrounding a hollow needle. The hub has a first seal (10) that engages sealingly with the connector. A slidable sleeve (8) slides over the needle in a first longitudinal direction from a first position in which the needle is fully or partially covered by the sleeve to a second position in which the needle is exposed to a third position in the second direction in which the needle is fully covered by the sleeve. A pack (9) having a closed end surrounds the hollow needle, hub and slidable sleeve. The pack has a first section which abuts the hub or the first seal to form a second seal and the pack has a second section which engages the needle tip to form a third seal (12) between the closed end of the pack and a needle tip.

17 Claims, 3 Drawing Sheets

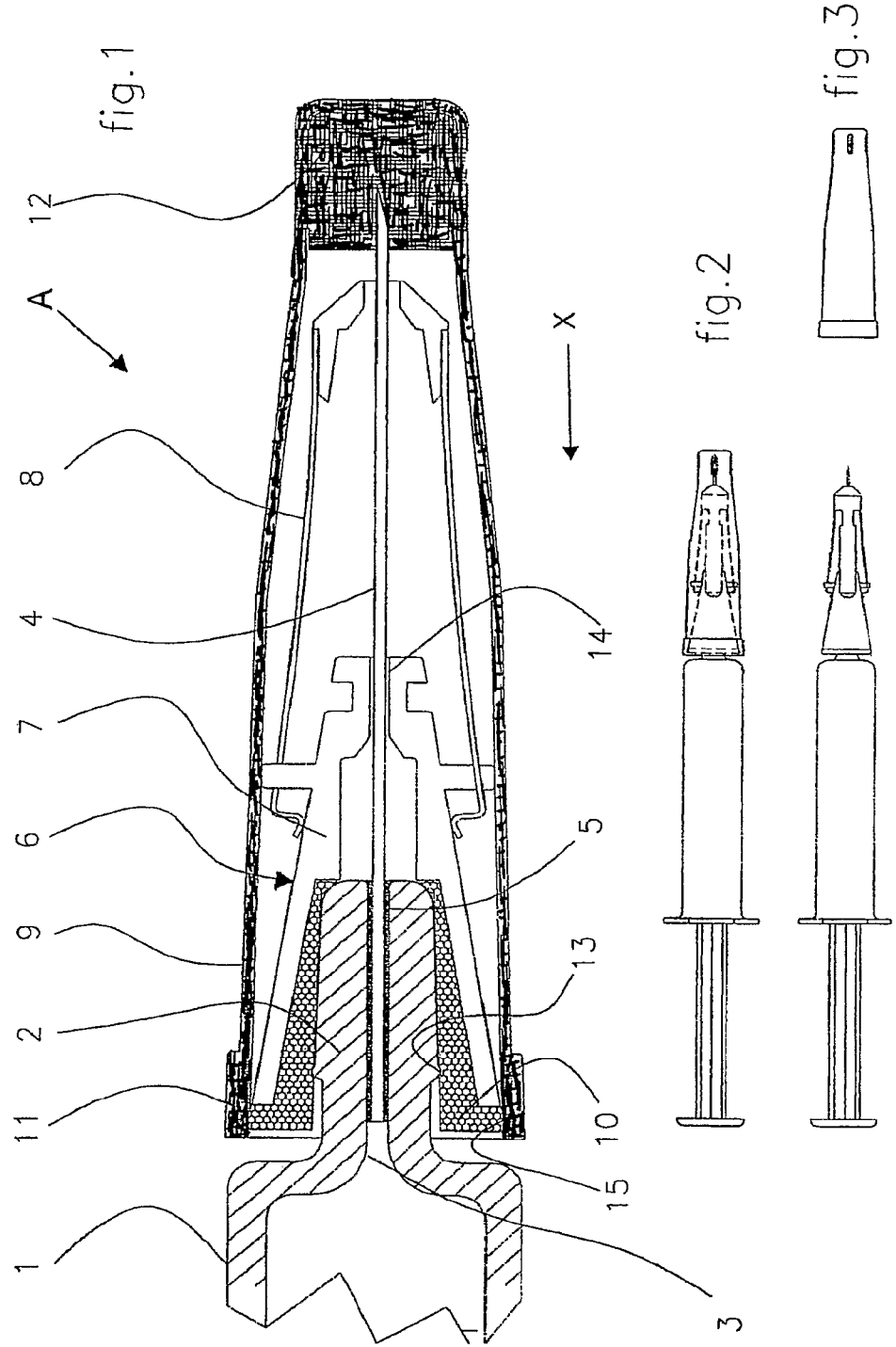

SAFETY NEEDLE ACCESSORY

CROSS-REFERENCE TO RELATED APPLICATION

This application is a Section 371 of International Application No. PCT/US2007/017455, filed Aug. 6, 2007, which was published in the English language on Feb. 7, 2008 under International Publication No. WO 2008/016710 A1, the disclosure of which is incorporated herein by reference.

This invention relates to a safety needle accessory and particularly to a safety needle accessory sealed with in a pack suitable for sealing pre-filled syringes.

Needle stick injuries carry a significant risk of spreading infection such as HIV and hepatitis, and are commonplace among healthcare workers. The USA has led the way in introducing legislation that obliges healthcare providers to use the safest devices when giving injections, intravenous drug administration and similar invasive procedures. Other countries are following, and even without legislation, the ever-present risk of litigation has alerted pharmaceutical companies and health authorities to seek suitable safe devices.

As a result of the heightened awareness of needle stick injuries, there have been a large number of inventions purporting to solve the problem. Most take the form of a protective sleeve which covers the needle tip after the injection has been given, or means for retracting the needle rapidly into the syringe barrel. In the former case, a weakness of the designs has been the need for the user to perform an action to render the needle safe; thus if the step is omitted, the risk remains. In the second case, the needle retraction mechanism requires that the syringe plunger is pushed to the end of its stroke in order to activate the retraction mechanism. In other words, virtually none of the devices are "fail safe". In many real-life situations, the patient can involuntarily react to the pain of the injection and pull away from the needle, exposing the sharp tip, and therefore presenting a risk of a needle stick.

Another drawback of prior art safety needles (which in the present context includes safety syringes) is that they are not compatible with current accepted practice. The problems includes drug incompatibility with the device construction materials, difficulty in using standard sterilising methods, difficulty in fitting to the syringe, large size, difficulty in filling, and very high cost.

A common requirement is for pre-filled syringes, and for reasons of drug compatibility and long-term storage, the syringe barrel is often made from glass, with the hypodermic needle bonded into the delivery end of the syringe barrel. Alternatively, a few drugs are compatible with plastics, and there are available plastic syringe barrels with moulded or bonded hypodermic needles. Hitherto, there have not been any successful combinations of pre-filled syringe with a bonded-in needle and a safety device to protect the user from suffering a needle-stick injury, and it is to this requirement the present invention is directed. One of the main reasons for the lack of commercial success is that the proposed new devices often include drug contact materials which do not have a safety and compatibility record, or have clumsy operating procedure, are too big, or incompatible with common filling techniques and so forth.

As stated hereinabove, there have been no successful safety needle and pre-filled syringe combinations, and the challenge is to meet the strict requirements of various sterilising methods, maintaining sterility of the drug and needle during storage, preventing loss of drug through thermal expansion, ease of use, and low cost.

Accordingly, the present invention provides a safety needle accessory comprising a hub for surrounding a hollow needle having a tip and having a connector for attachment to a syringe, wherein the hub has a first seal which engages sealingly with the connector,
a slidable sleeve adapted to slide over the needle in a first longitudinal direction from a first position in which the needle is fully or partially covered by the sleeve to a second position in which the needle is exposed, and in a second longitudinal direction from the second position to a third position in which the needle is fully covered by the sleeve, and a pack surrounding the hollow needle, hub and slidable sleeve having a closed end covering the needle and an open end exposing the connector of the hub,
wherein the pack is composed of an elastic material which is gas-permeable and impermeable to microorganisms and pyrogens, and wherein the pack has a first section which abuts the hub or the first seal to form a second seal, and wherein the pack has a second section which engages the needle tip to form a third seal between the closed end of the pack and the needle tip.

The present invention also provides an injection device comprising a syringe having a hollow needle attached thereto and a safety needle accessory as defined herein.

In a first preferred embodiment, a safety device as described in our co-pending patent application WO 2004/071560 is assembled to a syringe (i.e. barrel and plunger) having a bonded hypodermic needle, over which is fitted the safety device. A seal between the syringe and hub of the safety needle accessory is provided by a soft polymer. A pack encloses the syringe and safety device assembly, and has a rubber seal which seals against the periphery of the safety device hub, and further has a rubber seal which seals the opening of the hypodermic needle.

In a second preferred embodiment, which is similar to the first, the seal between the hub of the safety needle accessory and connector also seals directly to the pack, and the hypodermic needle seal is provided as before.

As an alternative to the previous embodiments, in a third embodiment, the safety device is bonded to the outlet connector of a syringe.

The present invention will now described with reference to the following drawings, in which:

FIG. 1 shows a longitudinal section on the centreline of a syringe and safety needle accessory in accordance with an embodiment of the present invention;

FIGS. 2 and 3 show an overall view of the syringe and safety needle accessory in accordance with the present invention with the pack attached and detached, respectively;

Unless stated otherwise, like parts are given like notation.

Figure 4:
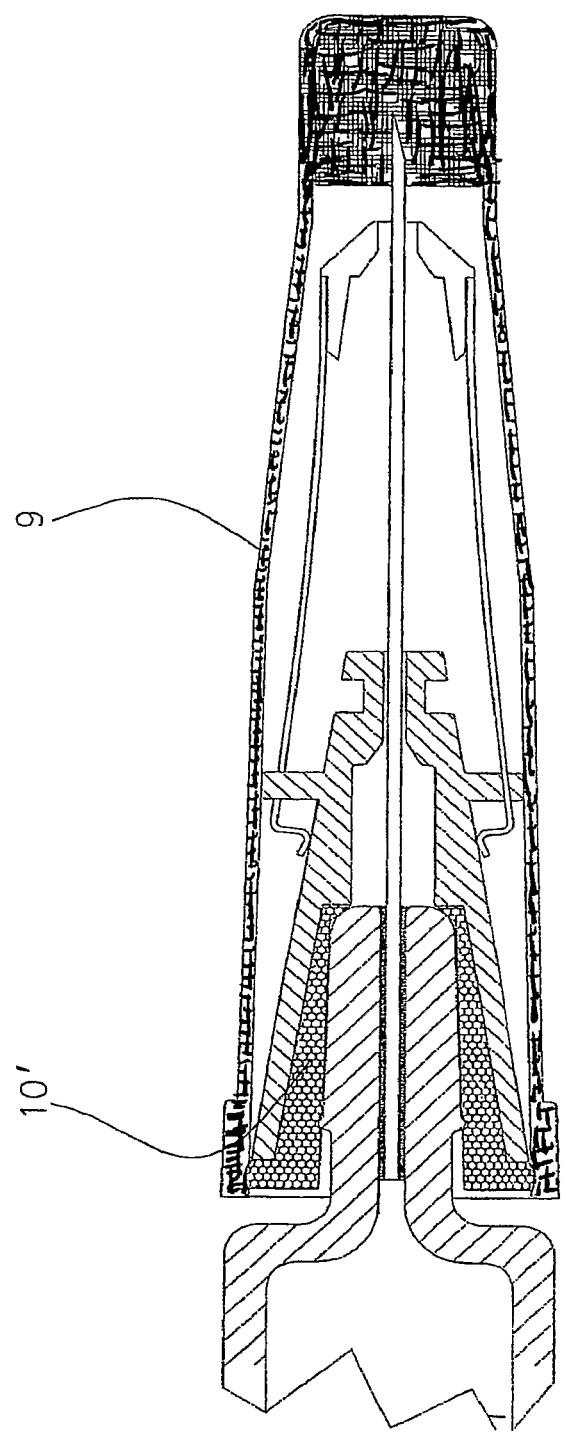
FIG. 4 shows a longitudinal section on the centreline of a syringe and safety needle accessory in accordance with a further embodiment of the present invention.

FIG. 1 shows an injection device A having a syringe 1 (only part of the syringe barrel is shown) having a connector 2. Connector 2 has a hole 3, into which is bonded with an adhesive 5 a hollow needle 4 permitting fluid communication between the syringe and the hollow needle 4. The syringe is often made from borosilicate glass, and the stainless steel needle may be bonded with an ultra-violet cured adhesive, this being a typical construction in common use. The safety needle accessory 6, which is more fully described in WO 2004/071560, has a hub 7 which surrounds the connector 2, and is fitted with slidable sleeve 8, although any other safety shield could be used. The sleeve 8 is arranged to operate when the needle device is pushed onto the patient's skin, by sliding along the hub in the direction of arrow X. When the device is withdrawn from the patient, the sleeve 8 slides back down the hub 7 until it locks in a position to prevent a needle stick injury. There are a number of devices which have been disclosed which achieve the same objective of preventing needle stick injuries, and the present invention may be adapted to suit the features peculiar to those devices, to achieve the same end.

In the present invention, the hub 7 has a hole 14 through which the needle 4 passes with clearance. Alternatively, however, the needle 4 could be bonded directly to the hole 14 (embodiment not shown). Hub 7 has an elastic seal 10 which engages sealingly with the connector 2. The connector 2 has a ridge 13 around its circumference, which locally increases the sealing force on the seal 10, and preferably prevents easy removal of the hub 7 and seal 10 from the connector 2. Thus, the elasticity of the seal provides frictional contact between the seal and the other component (here the connector on the syringe) such that a barrier to the ingress of bacteria and pyrogens is created.

To complete the protection of the drug and needle, a pack 9 is fitted over the safety device/syringe assembly. The pack 9 has a first section 11 which abuts the hub or the first seal to form a second seal. FIG. 1 show the first section 11 seal onto the rim 15 of the first seal 10.

Figure 5:
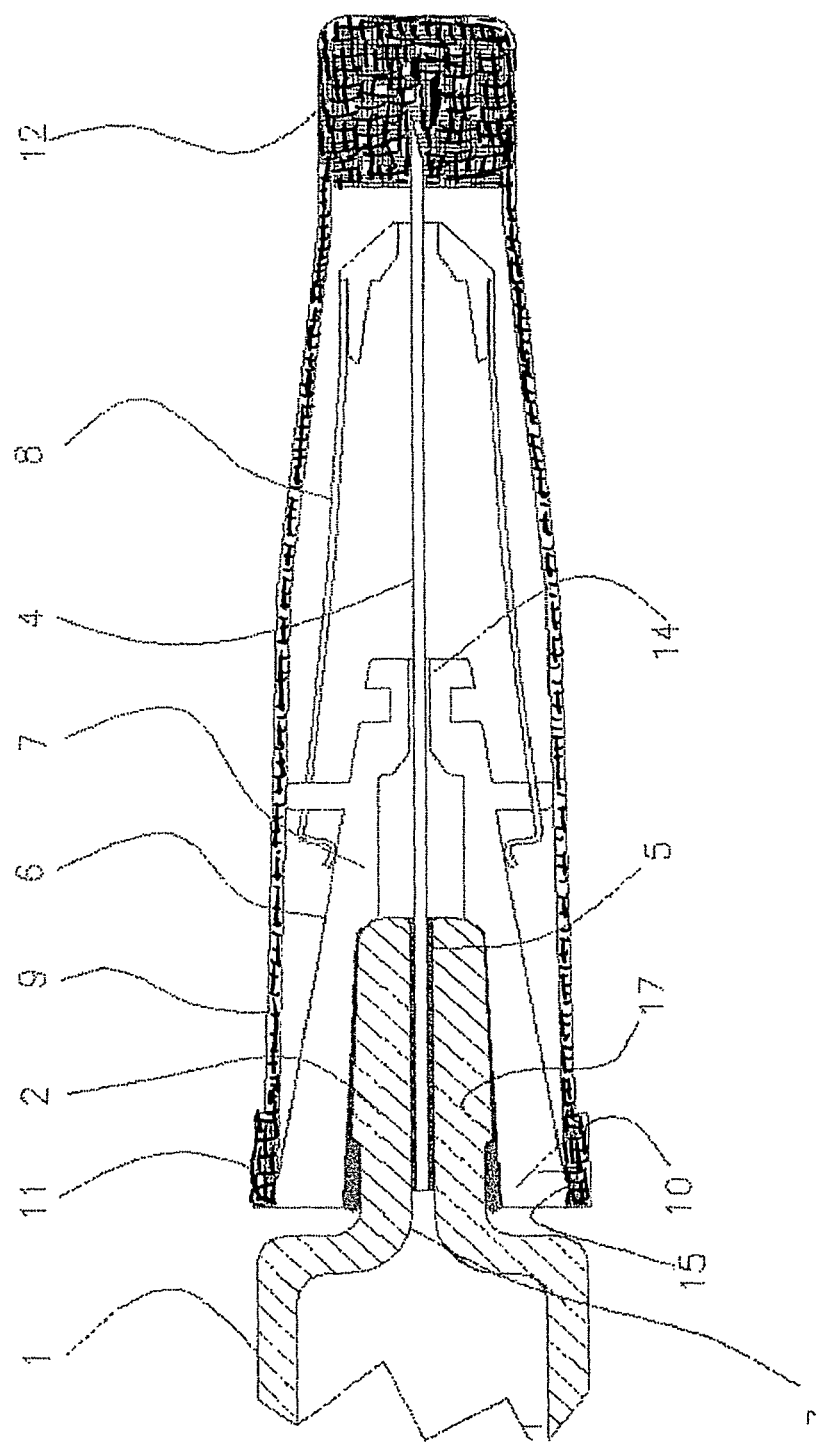
FIG. 5 shows a similar assembly to those illustrated in the other drawings in which the safety device is bonded to the syringe with an adhesive.

In addition, the pack has a second section 12 which engages the needle tip to form a third seal at the closed end of the pack 9, i.e. the end distal to the syringe, and seals the tip of the needle 4. The second section 12 is typically extended so that it is thicker than the rest of the pack 9, as shown in FIGS. 1, 4 and 5. Sealing is effected by the needle being position such that the tip penetrates the second section 12 of the pack 9. The third seal prevents loss or contamination of the injectate and prevents the contents of the syringe 1 from leaking during thermal expansion.

The pack 9 is preferably moulded from a low-density polyethylene or a rubber, and more preferably a pharmaceutical grade of sealing rubber such as iso-butyl rubber or isoprene, including blends of isoprene. This material is often used because it is a gas-permeable material which permits the passage of a sterilising gas, such as ethylene oxide, but prevents the passage of harmful bacteria and pyrogens. A common way of bulk packing syringes for pre-filling is to load them into holes in a plastic tray, so that the syringes hang by the finger flange. The loaded tray is placed into a plastic tub, and sealed by a permeable membrane. The sealed tub is subjected to a sterilising gas such as ethylene oxide, and then, after a period, ordinary atmosphere permeates through the membrane to displace the sterilising gas, and the membrane prevents the passage of bacteria. During this process, the sterilising gas also permeates through the rubber seals that protect the needle.

When it is preferable to avoid using ethylene oxide or other sterilising gas sterilise the assembly, other techniques such as by gamma radiation may be used, and since the sealing materials are not required to be permeable, may be made from other resilient or conformable materials, such as polyester elastomers.

The assembly is shown complete in FIG. 2, and in use, the pack 9 is withdrawn from the syringe/safety needle assembly, FIG. 3, and the injection is given. By incorporating seal 10 and the first and second sections 11 and 12, the ingress of contaminants (particularly microorganisms, e.g. bacteria, and pyrogens) into the pack 9 is prevented. The first seal 10 provides a seal between the connectors of the syringe 1 and hub 7 when the syringe is attached. The first section 11 provides a seal between the hub 7 and the interior rim 15 of the open end of the pack 9 when the pack is positioned over the hub 7.

FIG. 4 shows a very similar assembly, but in this case, the first seal 10 abuts against the inside of the pack 9.

Where the accessory is supplied separately from the syringe, the open end of the pack may be covered by a releasable membrane or cap.

FIG. 5 shows yet another alternative method of sealing the hub 7 to the connector 2 by an adhesive 17. Thus, in this embodiment the first seal 10 is an adhesive 17. The adhesive may be coated on the hub 7 and adheres to the syringe when the syringe connector is engaged with the hub connector. Preferably, the injection device is supplied with a pre-filled syringe adhered to the safety needle accessory. A suitable adhesive would be UV-cured or other rapidly setting adhesive compatible with the materials of construction.

In order to increase the strength of the pack 9 and to avoid damage to the accessory, the pack 9 may further comprise a rigid support (not shown in the Figs), which may be externally or internally applied to the pack 9. The support may be longitudinal ribs or a scaffold which surrounds the pack 9.

The present invention is compatible with current pre-filled syringe technology, including pre-filled reconstitution syringes, whereby a solvent is caused to mix with a lyophilised drug prior to administration.

In all embodiments, when the pack 9 is removed, the safety device remains on the syringe. The present invention is not limited to a precise mechanism of operation of the slidable sleeve. However, the slidable sleeve adapted to slide over the needle in a first longitudinal direction from a first position in which the needle is fully or partially covered by the sleeve to a second position in which the needle is exposed, and in a second longitudinal direction from the second position to a third position in which the needle is fully covered by the sleeve. Preferably the slidable sleeve has an elastically deformable portion and/or further comprises an elastically deformable member such that as the slidable sleeve is caused to move in the first direction towards the second position as the needle is injected into a patient, a resultant force is generated in the deformable portion or deformable member which causes the slidable sleeve to move towards the third (and first) position when the needle is removed from the patient, the safety needle accessory further comprising a locking mechanism capable of retaining the slidable sleeve in the third position after removal of the needle from the patient. The accessory may also further comprise engageable portions on the slidable sleeve and the hub to hold the sleeve in the first position where the sleeve is partially retracted and, when assembled with a syringe having a hollow needle, the needle is partially exposed. This allows the tip of the needle to be seen by the user prior to injection. This assists the user in guiding the needle for placement on the patient's skin or aspirating excess drug or air. Preferably the injection device of the present invention is supplied prior to use with the needle tip partially exposed. The pack is then removed and the needle injected into the patient. Further details are described in WO 2004/071560. Other safety devices intended to prevent or reduce needle-stick injuries, and which may employ a resiliently biased sliding sleeve (see, for example U.S. Pat. Nos. 4,813,940 and 5,104,384) may also be used with the accessory of the present invention.

The invention claimed is:

1. A safety needle accessory comprising:
   a hub for surrounding a hollow needle having a tip and having a connector for attachment to a syringe, wherein the hub has a first seal which engages sealingly with the connector,
   a slidable sleeve adapted to slide over the needle in a first longitudinal direction from a first position in which the needle is fully or partially covered by the sleeve to a second position in which the needle is exposed, and in a second longitudinal direction from the second position to a third position in which the needle is fully covered by the sleeve, the slidable sleeve including a distal end proximate the tip of the needle and an opposing free end proximate the connector, the free end of the slidable sleeve sliding over at least a portion of the hub when the slidable sleeve moves from the first position to the second position, and
   a pack surrounding the hollow needle, hub and slidable sleeve having a closed end covering the needle and an open end exposing the connector of the hub, wherein the pack is comprised of an elastic material which is gas-permeable and impermeable to microorganisms and pyrogens, and wherein the pack has a first section which abuts the hub or the first seal to form a second seal, and wherein the pack has a second section which engages the needle tip to form a third seal between the closed end of the pack and the needle tip, and
   wherein the needle tip extends past a distal end of the slidable sleeve in the first position in a pre-injection state.

2. The safety needle accessory as claimed in claim 1, wherein the first seal is an elastic seal.

3. The safety needle accessory as claimed in claim 1, wherein the pack is comprised of an iso-butyl rubber or iso-prene.

4. The safety needle accessory as claimed in claim 1, wherein at least one of the first seal and the pack is comprised of low-density polyethylene or a rubber.

5. The safety needle accessory as claimed in claim 1, wherein the first seal is an adhesive.

6. The safety needle accessory as claimed in claim 1, wherein the pack is substantially tubular.

7. The safety needle accessory as claimed in claim 1, wherein the open end of the pack is covered by a releasable membrane or cap.

8. The safety needle accessory as claimed in claim 1, wherein the pack further comprises a rigid support.

9. The safety needle accessory as claimed in claim 1, wherein the slidable sleeve has an elastically deformable portion or further comprises an elastically deformable member such that as the slidable sleeve is caused to move in the first direction, a resultant force is generated in the deformable portion or deformable member which causes the slidable sleeve to move in the second direction when the needle is removed from a patient.

10. The safety needle accessory as claimed in claim 1, further comprising a locking mechanism capable of retaining the slidable sleeve in the third position after removal of the needle from a patient.

11. The safety needle accessory as claimed in claim 1, the needle is partially exposed in the first position.

12. The safety needle accessory as claimed in claim 1, wherein the hollow needle is attached to the hub.

13. An injection device comprising a syringe having a hollow needle attached thereto and a safety needle accessory as claimed in claim 1.

14. The injection device as claimed in claim 13, wherein the syringe is pre-filled with an injectable composition.

15. The injection device as claimed in claim 13, wherein the syringe is a pre-filled reconstitution syringe containing a lyophilised drug.

16. The injection device as claimed in claim 13, wherein prior to use the needle is partially exposed in the first position.

17. The injection device as claimed in claim 1, wherein the free end of the slidable sleeve moves radially outwardly along an exterior surface of the hub as the slidable sleeve moves from the first position to the second position.

* * * * *